US007002140B2

(12) United States Patent
Elsegood et al.

(10) Patent No.: US 7,002,140 B2
(45) Date of Patent: Feb. 21, 2006

(54) ULTRAVIOLET WATER TREATMENT SYSTEM

(75) Inventors: Christopher J. Elsegood, Bayfield (CA); Robert Joseph Drysdale, Goderich (CA); L. Michael Roberts, Goderich (CA)

(73) Assignee: Fibro Light Technology Inc., Goderich (CA)

( * ) Notice: Subject to any disclaimer, the term of this patent is extended or adjusted under 35 U.S.C. 154(b) by 0 days.

(21) Appl. No.: 10/770,517

(22) Filed: Feb. 4, 2004

(65) Prior Publication Data

US 2005/0167611 A1 Aug. 4, 2005

(51) Int. Cl.
*A61L 2/10* (2006.01)
(52) U.S. Cl. ............. 250/251; 250/435; 250/365; 250/431; 250/432 R; 210/748; 422/24

(58) Field of Classification Search ............... 250/251, 250/432 R, 365, 431; 210/748; 422/24
See application file for complete search history.

(56) References Cited

U.S. PATENT DOCUMENTS

| 4,103,167 A * | 7/1978 | Ellner ............... 250/432 R |
| 6,524,529 B1 * | 2/2003 | Horton, III ............ 422/24 |
| 2005/0000911 A1 * | 1/2005 | Thorpe ............... 210/748 |

* cited by examiner

*Primary Examiner*—Nikita Wells
*Assistant Examiner*—Zia R. Hashmi
(74) *Attorney, Agent, or Firm*—Borden Ladner Gervais, LLP; Jeffrey W. Wong

(57) ABSTRACT

An ultraviolet water treatment system comprising a water chamber having a water intake for untreated water to enter the chamber, and a water outlet for water to leave the chamber; an ultraviolet light source; and a fibre optic rod having a distributing end and a receiving end, the receiving end is located to receive the focused ultraviolet light from the light source and convey the light through the rod and out the distributing end into the chamber to treat the water.

19 Claims, 6 Drawing Sheets

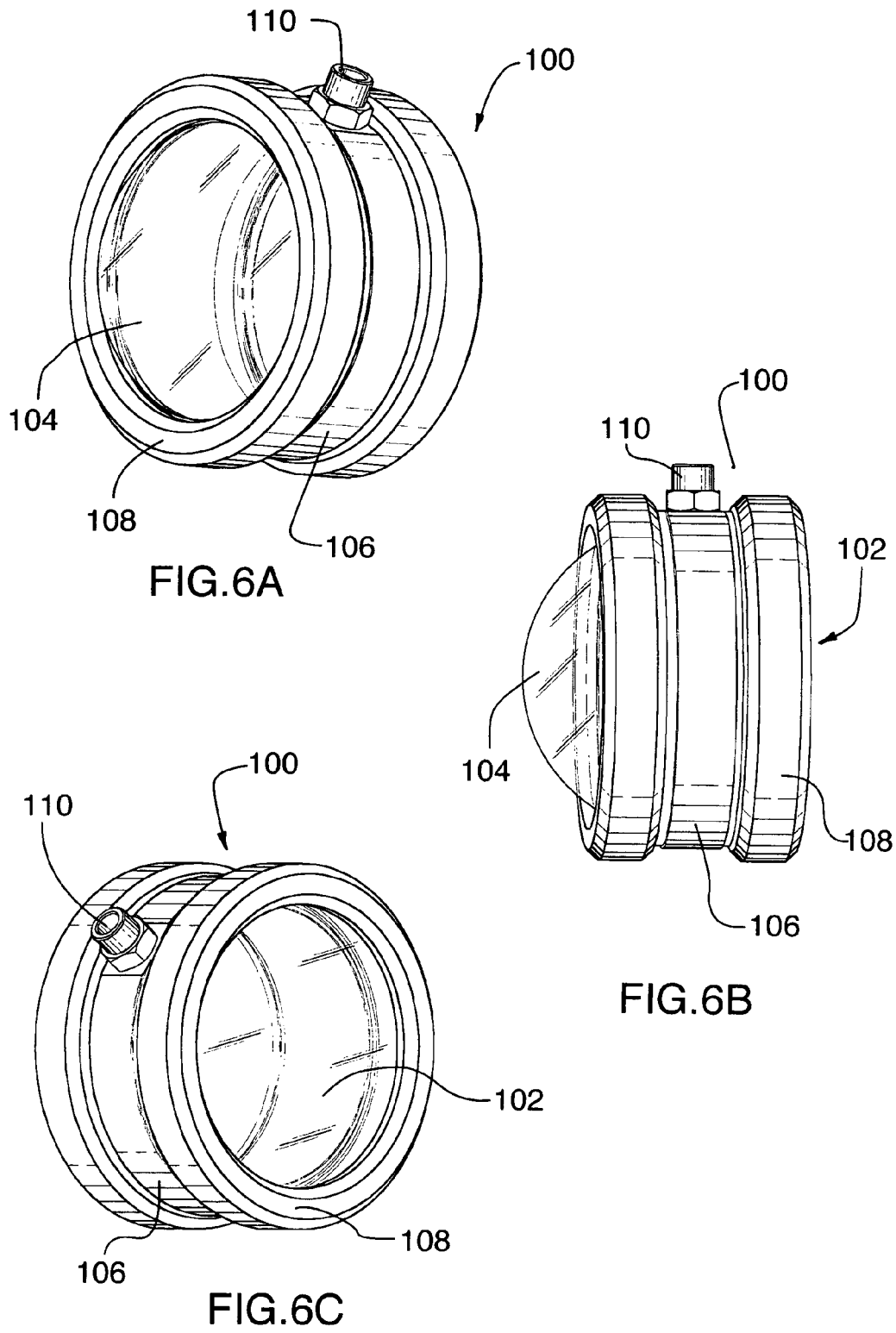

ULTRAVIOLET WATER TREATMENT SYSTEM

FIELD OF THE INVENTION

The invention relates generally to water treatment systems. More particularly, the invention relates to water treatment systems employing ultraviolet light.

BACKGROUND OF THE INVENTION

With ultraviolet light, light and temperature can be precisely controlled to create an atmosphere for sterilization and purification of water. Of all the different characteristics of ultraviolet light, selection of a proper wavelength for use is generally most important. Natural light is an optimum light in the area of ultraviolet as in sunlight, however, in many areas an artificial supplement of ultraviolet light in a higher range may be realized.

Natural light and artificial light have different wavelengths or spectral qualities. There are many different types of artificial light depending on the light source used and the characteristics. The spectral characteristics can be altered or enhanced by the use of filters, coating or other means. Normally, the violet-blue segments of the spectrum are most important for sterilization and purification production.

A plethora of lighting systems for ultraviolet sterilization and purification are currently in use such as the one described in Canadian Patent No. 2,373,673, entitled Flow Cytometer and Ultraviolet Disinfecting Systems which was published on Aug. 27, 2002. In almost all cases, a high amount of light output results in considerable heat generated near the source and transferred into the water. As required, the light source can be placed close to the treated area. Significant temperature change develops near the water which can produce dangerous results. Light sources that have been used in the past include fluorescent ultraviolet lighting, high or low pressure lights and a variety of others.

Often times, water lighting systems must deal with excessive heat produced by existing technologies. Water lighting systems allow the placing of light sources close to the treatment area. The drawback is the heat build up around the light in conjunction with electricity is detrimental. This light intensity is very high to ensure the maximum rate of sterilzation and purification will occur. The water jacket enclosure surrounds the bulb and absorbs a percentage of ultraviolet light to the treatment area. The result is a reduction of light output through the surface.

Many disadvantages of the current systems are heat output, complexity, cost and difficulty of maintenance operations. Heat values with electricity are the most problematic.

It is, therefore, desirable to provide a water treatment system which overcomes some of the disadvantages of the prior art.

SUMMARY OF THE INVENTION

It is an object of the invention to obviate or mitigate at least one disadvantage of previous water treatment systems.

In a first aspect, the present invention provides an ultraviolet water treatment system comprising a water chamber having a water intake for untreated water to enter the chamber, and a water outlet for water to leave the chamber; an ultraviolet light source; and a fibre optic rod having a distributing end and a receiving end, wherein the receiving end is located to receive a focused ultraviolet light from the light source and convey the light through the rod and out the distributing end into the chamber to treat the water.

The UV water treatment system is directed at being installed in existing water plumbing in houses, cottages etc.; where water needs to be treated/sterilized before use.

Other aspects and features of the invention will become apparent to those ordinarily skilled in the art upon review of the following description of specific embodiments of the invention in conjunction with the accompanying figures.

BRIEF DESCRIPTION OF THE DRAWINGS

Embodiments of the invention will now be described, by way of example only, with reference to the attached Figures, wherein:

FIGS. 6a, 6b and 6c are views of a second embodiment of the fibre optic rod of FIG. 4.

DETAILED DESCRIPTION

Generally, the invention provides an ultraviolet water treatment system for treating water for personal use.

Figure 1:
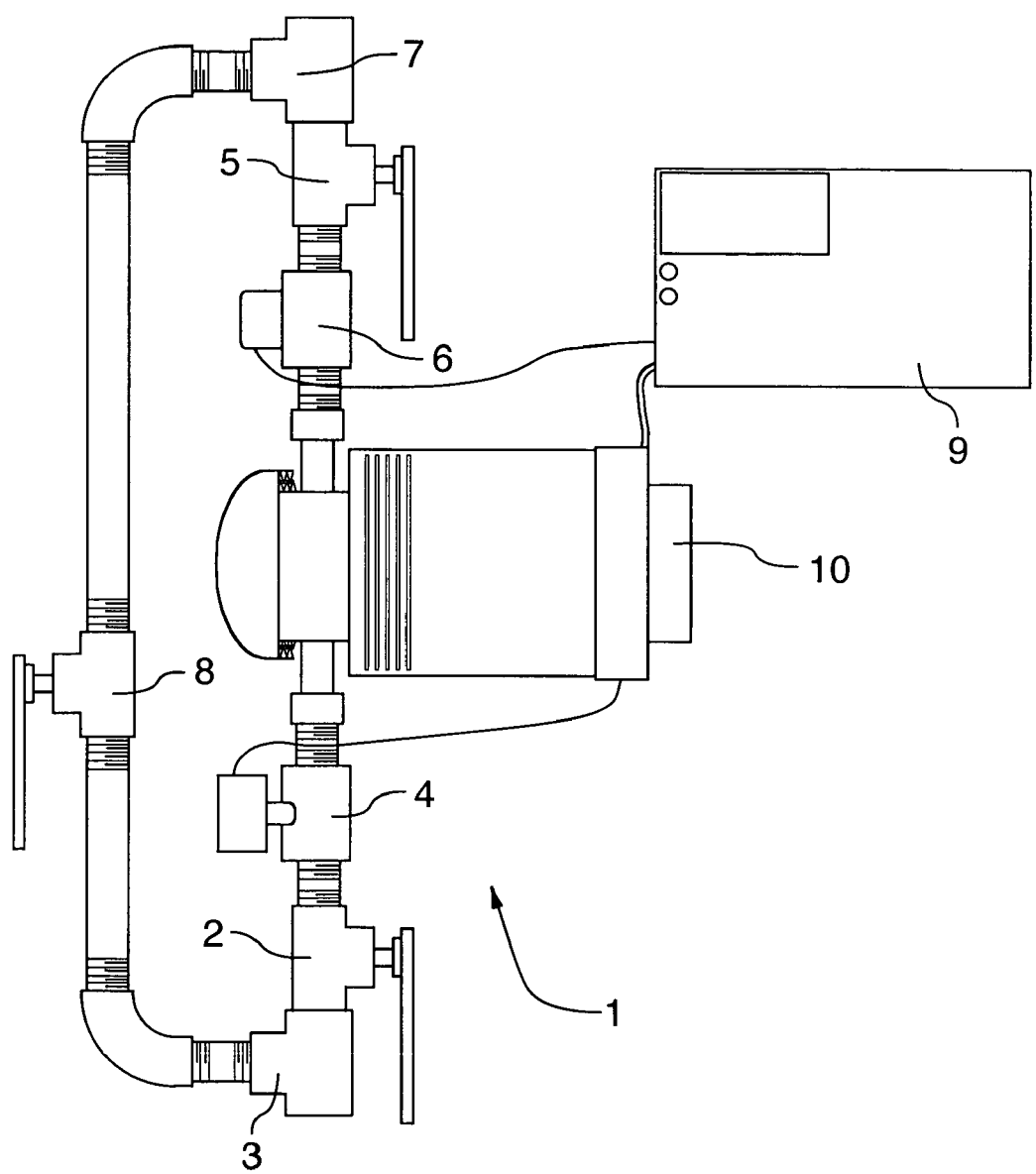
FIG. 1 is a schematic view of a water system.

Turning to FIG. 1, a schematic diagram of an ultraviolet water treatment system 10 installed in a water flow system is shown. The water flow system 1 comprises a water input (in which untreated water enters) which is connected to a shutoff valve 2 via a bypass T 3. The bypass T 3 is connected to a solenoid valve 4 which is connected to the water treatment system 10. The water treatment system 10 is then connected to a second shutoff valve 5 via a pressure/flow switch 6. The second shutoff valve 5 is connected to a second bypass T 7 which allows the treated water to be transferred to a requesting tap in the water system. The two bypass Ts 3 and 7 are connected to each other by a bypass valve and line 8. A power supply 9 is also connected to the UV water treatment system 10 the solenoid valve 4 and the pressure/flow switch 6.

Figure 2:
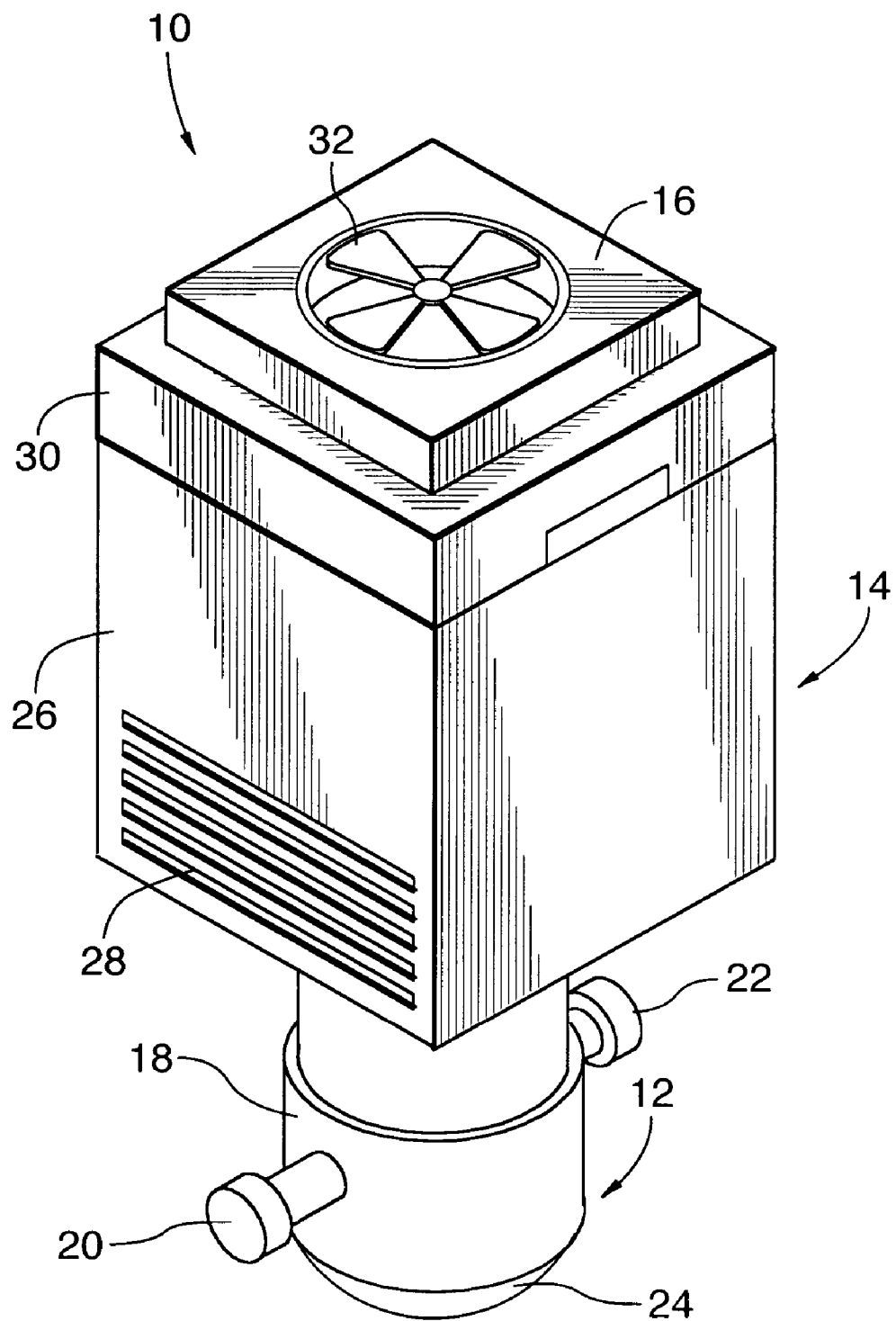
FIG. 2 is a perspective view of a first embodiment of a water treatment system.

Turning to FIG. 2, a perspective view of the ultraviolet water treatment system is shown. The water treatment system 10 generally comprises a water treatment section 12, a lamp housing section 14 and a ventilation section 16.

The water treatment section 12 comprises a water treatment chamber 18 preferably manufactured from stainless steel, connected to a water intake 20 and a water outlet 22. The water intake 20 and the water outlet 22 are both channel milled into the water treatment chamber 18. The water treatment section 14 also comprises a cap 24 which is removable to facilitate cleaning of the water treatment chamber 18. The cap 24 is screwably attached to the water treatment chamber 18 for easy removal/replacement.

The lamp housing section 14 comprises a body section 26 (having a set of ventilation vents 28 on opposite sides) and a cover 30 atop which the ventilation section 16 sits. The cover 30 may be removed from the top of the lamp body section 26 in order to repair any parts which are housed by the lamp housing section 14. These parts will be described in more detail below.

The ventilation section 16 houses a forced air ventilation fan 32 which is used to cool the inside of the lamp housing section 14 when the water treatment system 10 is in use. In general, the ventilation fan 32 is integrated into the top cover and is not removable on it's own.

Figure 3:
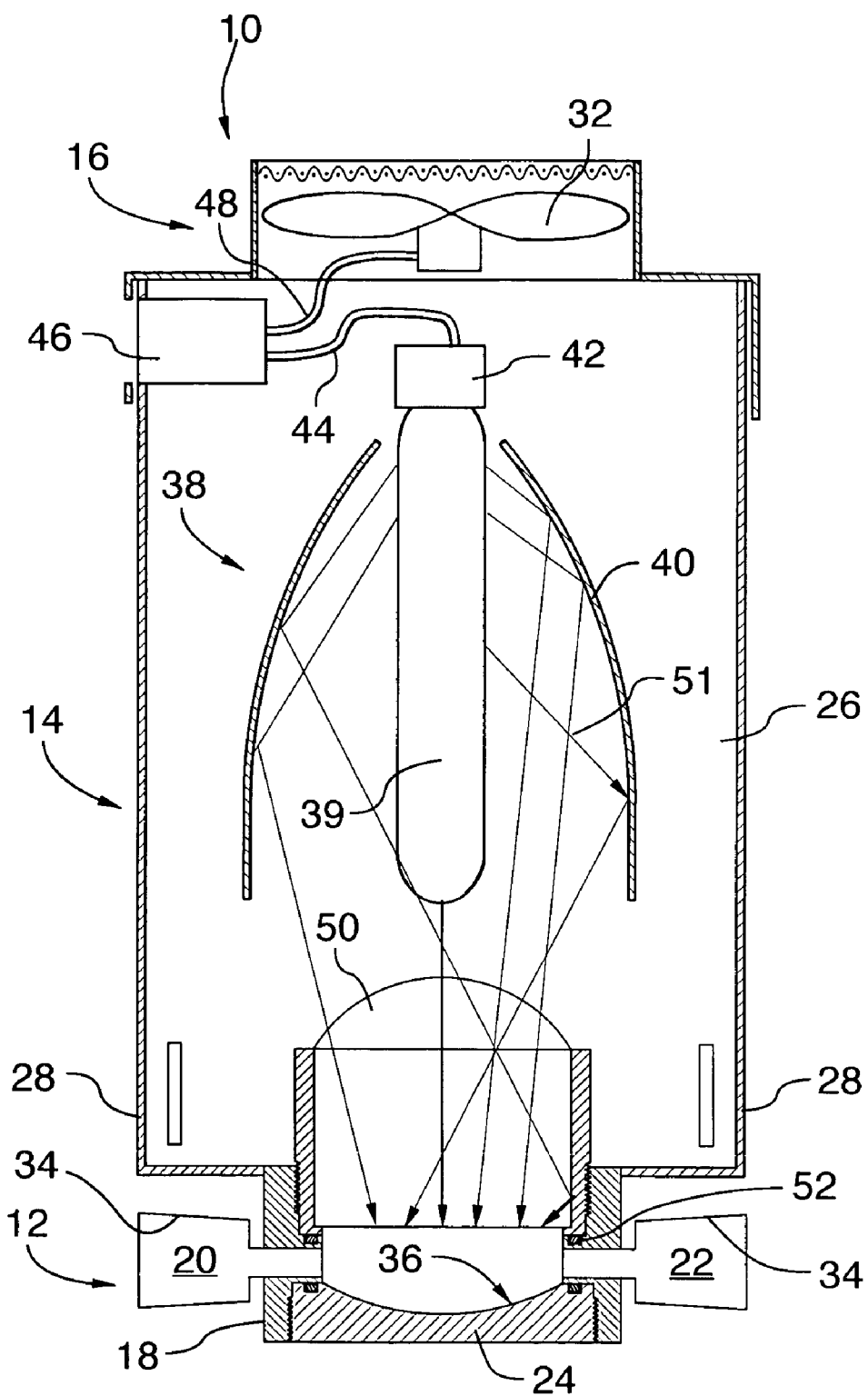
FIG. 3 is a sectional view of the water treatment system of FIG. 2.

Turning to FIG. 3, a sectional view of a first embodiment of the ultraviolet (UV) water treatment system 10 is shown. When installed, the water intake 20 and the water outlet 22 are generally attached, via their connectors 34, to standard plumbing parts in the water system. The cap 24 preferably has a polished reflective surface on its internal surface 36 facing the water treatment chamber 18 in order to assist in sterilization of the water. The internal surface 36 is preferably concave with a radius ground into it.

The lamp housing section 14 houses a UV source 38 comprising a UV lamp 39 for providing the necessary UV light to sterilize the water, a reflector 40, preferably a spun aluminium reflector which is used to focus the UV light and a lamp socket 42. The reflector may also be a dichroic ellipsoidal reflector. If any part of the UV source 38 breaks down, the entire UV source 38 is preferably replaced in order to maintain positional relationship between the UV lamp 39 and that reflector 40. The lamp socket 42 is connected via wiring 44 to a power supply connector 46 for providing power to the lamp 39. The power supply connector 46 is also connected by wiring 48 to the forced air ventilation fan 32 in the ventilation section 16. As will be understood by one skilled in the art, the power supply connector 46 is connected to the power supply 9.

At one end of the lamp housing body section 26 (near the water treatment chamber 18) is a UV conducting fibre optic rod 50, which, in the present embodiment, is made of quartz. The fibre optic rod 50 provides a connection between the water treatment section 12 and the lamp housing section 14 as will be described in more detail below with respect to FIG. 3. As can be seen, the optic rod 50 is preferably screwed into the water treatment chamber 18 with O-ring 52 to assist in sealing the connection. The O-ring 52 is preferably groove machined into the water treatment chamber 18 so that the rod 50 may be screwed down until the O-ring 52 is compressed thereby accurately locating the fibre optic rod 50 at a predetermined distance from the cap 24.

Located near the ventilation vents 28 are a pair of light traps 54 which assist in covering the vents 28 so that the UV light from the UV lamp 34 does not escape the lamp housing body 26, but is focused towards the fibre optic rod 50, during the sterilization process. As described above, the reflector 40 also assists in focussing the UV light towards the fibre optic rod 50 in order to provide maximum UV light to the rod 50 and therefore the sterilization process, as illustrated by the arrows 51, during the sterilization process.

The arrows 51 provide a schematic ray diagram showing various paths taken by the UV light from the lamp and the reflector during the sterilization process. After the UV lamp is powered on, the UV light rays reflect off the reflector towards the second optical end of the fibre optic rod. The UV light rays then travel from the second optical end to the first optical end via the middle section of the rod. The resultants rays fill up the lens at the first optical end which then transfers the UV rays into the water treatment chamber whereby the water is treated by the UV rays and sterilized.

Figure 4:
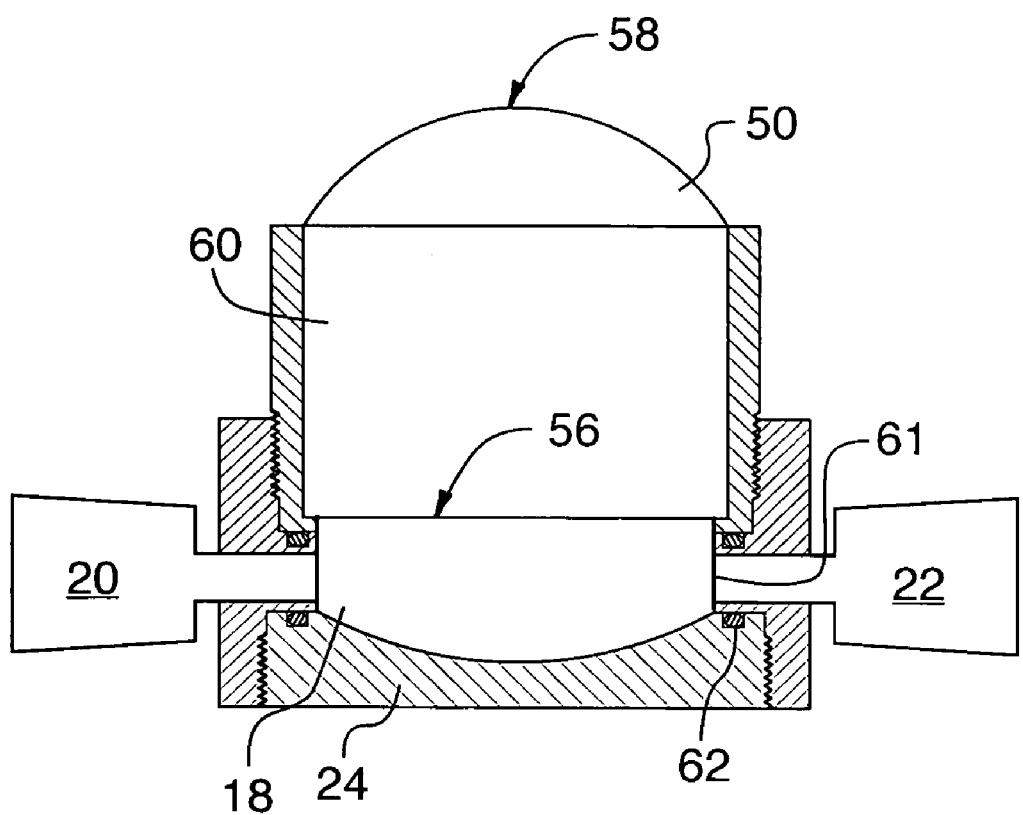
FIG. 4 is a sectional view of a fibre optic rod connected to a water treatment chamber in accordance with the water treatment system of FIG. 2.

Turning to FIG. 4, a more detailed schematic of the connection between the first embodiment of the fibre optic rod 50 and the water treatment chamber 18 is shown.

The fibre optic rod 50 comprises a first optical end 56 where an optical lens is ground into the fibre optic rod and covered with an infra-red (IR) reflective coating and a rounded second optical end 58 made from quartz. The quartz used in the second optical end 58 is preferably a high grade UV transmitting quartz such as surpasil quartz. Furthermore, the first optical end 56 may also be manufactured out of suprasil quartz. The second optical end collects UV light from the UV lamp 49 and the reflector 40 and concentrates it for transmission into the water chamber.

The optical lens used in the first optical end 56 may also be quartz. A middle section 60 of the rod 50, between the two optical ends 56 and 58, is manufactured out of quartz which causes the fibre optic rod 50 to be a quartz rod.

The optical ends and the middle section are held in place by a cylindrical sleeve 61, preferably manufactured out of stainless steel.

In an alternative embodiment, the rod 50 may be tapered in order to fit and seal in the opening between the lamp housing body section 26 and the water treatment chamber 18 rather than being screwed in. In this manner, the rod 50 is adhesively bonded to the chamber 18.

An O-ring 62 is also located between the cap 24 and the water treatment chamber 18 to seal the connection between the cap 24 and the chamber 18 so that no water may escape from the chamber before, during and after the sterilization process.

Figure 5A:
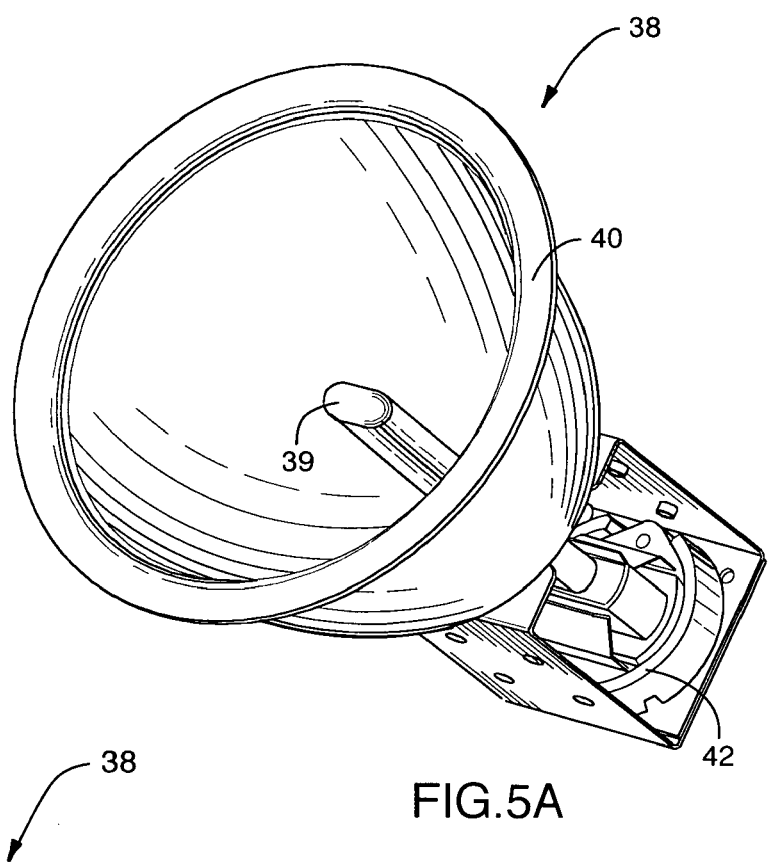
FIGS. 5a and 5b are views of an ultraviolet (UV) source for use in the water treatment system.
Figure 5B:
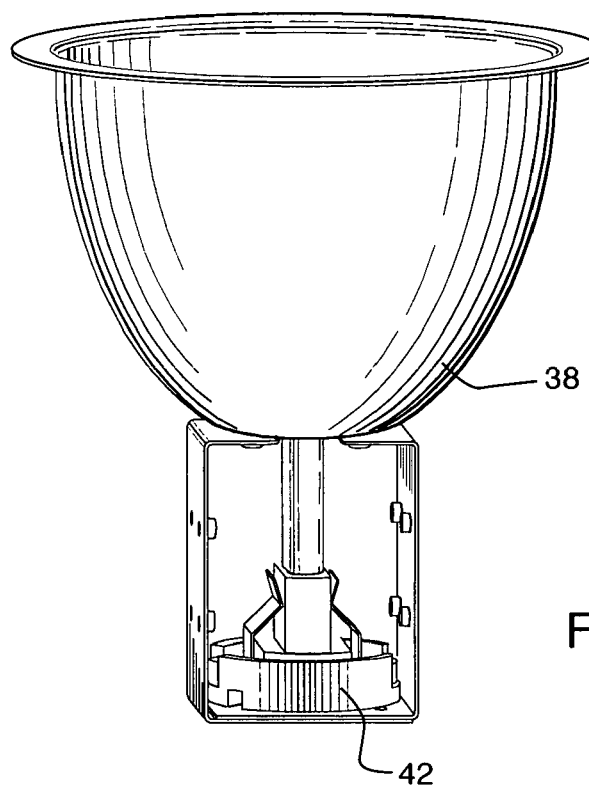

Turning to FIGS. 5a and 5b, a perspective view and a front view of the UV source 38 are shown. As can be seen in FIG. 5a, the UV lamp 39 is located centrally within the dichroic reflector 40. The position of the lamp 39 with respect to the reflector 40 is quite important since the dichroic reflector is used to reflect/focus the UV light directly onto the second optical end 58 of the fibre optic rod 50. If the lamp 39 is not centrally located, the impact of the focussed light is lessened. Therefore, when either the reflector 40 or UV lamp 39 needs to be replaced, in order to maintain the spatial relationship between the lamp 39 and the reflector 40, the entire UV source 38 is replaced and the wiring (not shown) is plugged into the lamp socket 42 of the new UV source.

Turning to FIGS. 6a, 6b and 6c, schematic views of a second embodiment of the fibre optic rod 100 are shown. As with the fibre optic rod described with respect to FIG. 4, the fibre optic rod 100 comprises a first optical end 102 and a second optical end 104 connected together by a middle section 106. As with the first embodiment, the first optical end 102, the second optical end 104 and the middle section 106 are housed in a stainless steel sleeve 108. In this embodiment, the middle section 106 comprises an index matching fluid which has optical qualities which are similar to quartz. In one embodiment, this index matching fluid is de-ionized water such that even if some of the index matching fluid was to escape or leak from the rod 100, there are little or no health risks associated with the de-ionized water which provides further health benefits for using the water treatment system. The index matching fluid transmits and converges the UV light rays from the lamp 39 and the reflector 40 as if the rod was an entirely solid quartz optical rod as described above.

There is also an air ballast 110 connected to the middle section 106 of the rod 100. The air ballast 110 is generally used to connect to a pump for insertion of the index matching fluid into the middle section 106. The air ballast 110 also allows for expansion of the index matching fluid during the sterilization process since the fluid generally expands when subjected to heat such as from the UV light. Therefore, the air ballast 110 protects the fibre optic rod from exploding due to the increased pressure in the liquid during the sterilization process.

As with the first embodiment, the fibre optic rod 100 is screwed into the water treatment chamber 18 with the air ballast being located within the lamp housing body. Due to the presence of the air ballast, the level of index matching fluid in the middle section 106 of the rod 100 does not change since the amount of fluid which changes to gas during the sterilization process returns to a liquid form once the UV light is powered off. Therefore, in general, once the fibre optic rod has been installed in the water treatment system 10 there is little or no requirement to pump extra index matching fluid into the rod. The insertion of the index matching fluid takes place before the rod is connected with the water treatment chamber 18.

Furthermore, due to a requirement that the air ballast 108 is required to be in a vertical position during use, in this embodiment of the water treatment system 10 the system is installed in the water system with the axis of the water intake, the water treatment chamber and the water outlet forming a line perpendicular to the ground.

In operation, the optic rod gathers the UV light in its second optical end and then conveys this light to the water while also acting to absorb/deflect infra-red rays from being transmitted into the water.

In one embodiment of operation, seen as an always-on embodiment, the water treatment system 10 is initially powered up by connecting the power supply connector 46 to the power supply 9. This provides power to the treatment system 10 allowing for the forced air ventilation fan 32 to operate along with the UV lamp 39. The forced air ventilation fan 32 operates to cool the inside of the lamp housing body 26 of the lamp housing section 14 since there is a high amount of heat generated by the UV lamp 39 during the sterilization process by drawing in atmospheric air through the ventilation slots 28 and up through the body section 14 to the fan section where the air exits out at the top of the water treatment system 10 thereby passing the UV lamp and the socket.

After the treatment system 10 is powered up, the UV lamp 39 also turns on. The UV light generated by the UV lamp 39 is then focussed by the reflector 40 at the second optical end 58 of the fibre optic rod 50. The UV light is also trapped in the lamp housing body section 26 via the light traps 54 located in front of the ventilation vents 28 and directed at the second optical end 58. The UV light is focussed at the second optical end 58 of the fibre optic rod 50 which then conveys the light through the middle section 60 to the first optical end 56 near the water treatment chamber 18. The middle section, either the solid quartz rod or the index matching fluid act to reduce the heat being transmitted to the water treatment chamber from the UV lamp.

While the UV light heats up the fibre optic rod 50 untreated water travels into the water treatment chamber 18 via the water intake 20 to the water treatment chamber 18 where it is subjected to the UV light emitted by the first optical end of the fibre optic rod 50 which sterilizes the untreated water. In some cases, the water in the water treatment chamber may also contact the first optical end 56 of the fibre optic rod 50 without affecting the sterilization process. The treated water then travels out of the water treatment chamber 18 via the water outlet 22 where the water is then transferred for use.

In another embodiment of operation, seen as an on-demand embodiment, the UV source and the fan are initially unpowered. Once a flow sensor, located in the water outlet 22, senses a request for treated water (i.e. a tap opening), a signal is sent to a processor which causes a gate, located between the water intake 20 and the water treatment chamber 18 to close in order to prevent further untreated water from entering the chamber and holds this water in the water intake 20. The processor then sends a signal to power up the ventilation fan 32 and the UV source 38. Once the fan and the source have been powered up (after a slight delay), a signal is sent to the gate to open allowing the untreated water to flow from the water intake 20 to the chamber 18 to be treated. After the water is treated, the water travels from the water outlet to the tap requesting the treated water. Once the tap is closed, the flow sensor senses this and sends a signal to the processor to power down the UV source and the ventilation fan 32 and close the gate once again.

One advantage of the water treatment system 10 is that the first embodiment (with a fibre optic rod manufactured entirely from quartz) may be installed either horizontally or vertically in the water system 1. However, with the second embodiment of the water treatment system having the middle section of the fibre optic rod comprising an index matching fluid, the water treatment system must be installed with the axis of the water intake, water treatment chamber and the water outlet in a vertical position.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. An ultraviolet water treatment system comprising:
   a water chamber having a water intake for untreated water to enter said chamber, and a water outlet for water to leave said chamber;
   an ultraviolet light source; and
   a fibre optic rod having a distributing end and a receiving end, said receiving end being located to receive said ultraviolet light from said light source and convey said light through said rod and out said distributing end into said chamber to treat said water.

2. An ultraviolet water treatment system as claimed in claim 1, wherein said ultraviolet light source has a reflector for focusing said ultraviolet light at said distributing end.

3. An ultraviolet water treatment system as claimed in claim 2 wherein said ultraviolet light is focussed at a remote focal point in said distributing end.

4. An ultraviolet water treatment system as claimed in claim 3, wherein said receiving end of said fibre optic rod is located at said remote focal point.

5. An ultraviolet water treatment system as claimed in claim 4, wherein said reflector is ellipsoidal in shape and axially disposed around said light source.

6. An ultraviolet water treatment system as claimed in claim 1, wherein said receiving end has an optical lens for further focusing said ultraviolet light.

7. An ultraviolet water treatment system as claimed in claim 1, wherein said ultraviolet light source is housed in a light chamber attached to and having an opening to said water chamber, said opening through which said receiving end of said fibre optic rod is situated whereby said distributing end is situated in said water chamber.

8. An ultraviolet water treatment system as claimed in claim 7, wherein said rod is tapered to fit and seal in said opening.

9. An ultraviolet water treatment system as claimed in claim 8, wherein said rod is tapered by 5 degrees.

10. An ultraviolet water treatment system as claimed in claim 9, wherein said rod is secured in said opening with an adhesive bond.

11. An ultraviolet water treatment system as claimed in claim 7, wherein said light chamber has ventilation means.

12. An ultraviolet water treatment system as claimed in claim 1, wherein said fibre optic rod is quartz.

13. An ultraviolet water treatment system as claimed in claim 1, wherein said fibre optic rod comprises an index matching fluid.

14. An ultraviolet water treatment system as claimed in claim 13, wherein said index matching fluid is de-ionized water.

15. An ultraviolet water treatment system as claimed in claim 13, wherein said fibre optic rod further comprises an air ballast.

16. An ultraviolet water treatment system as claimed in claim 1, wherein said water chamber has a reflective interior surface.

17. An ultraviolet water treatment system as claimed in claim 1, wherein said water chamber has a removable portion for access into said water chamber.

18. An ultraviolet water treatment system as claimed in claim 1, wherein said rod has a rod body having an optical lens in said receiving end for focusing said ultraviolet light into said rod and a lens in said distributing end to transmit and concentrate said ultraviolet light into the water for treatment.

19. An ultraviolet water treatment system as claimed in claim 2 wherein said reflector is one of a dichroic reflector or a spun aluminium reflector.

* * * * *